United States Patent
Sevenants et al.

(10) Patent No.: US 11,065,589 B2
(45) Date of Patent: Jul. 20, 2021

(54) RADIALLY DRIVEN AGITATOR

(71) Applicant: Pall Corporation, Port Washington, NY (US)

(72) Inventors: Jorrit Sevenants, Tienen (BE); Stefanus Van Den Berghe, Antwerp (BE)

(73) Assignee: PALL CORPORATION, Port Washington, NY (US)

(*) Notice: Subject to any disclaimer, the term of this patent is extended or adjusted under 35 U.S.C. 154(b) by 477 days.

(21) Appl. No.: 16/214,395

(22) Filed: Dec. 10, 2018

(65) Prior Publication Data

US 2020/0179885 A1 Jun. 11, 2020

(51) Int. Cl.
*B01F 13/08* (2006.01)
*A61J 1/20* (2006.01)
*B01F 15/00* (2006.01)

(52) U.S. Cl.
CPC ............ *B01F 13/0854* (2013.01); *A61J 1/20* (2013.01); *B01F 15/00688* (2013.01); *B01F 2215/0073* (2013.01)

(58) Field of Classification Search
CPC .............. B01F 13/0845; B01F 13/0854; B01F 13/00872
USPC ................................................. 366/273, 274
See application file for complete search history.

(56) References Cited

U.S. PATENT DOCUMENTS

| | | | | |
|---|---|---|---|---|
| 1,847,006 A | * | 2/1932 | Kalischer | H02K 49/02 310/104 |
| 3,279,765 A | * | 10/1966 | Sato | B01F 13/0827 366/273 |
| 3,572,651 A | * | 3/1971 | Harker | B01F 13/0863 366/185 |
| 4,993,841 A | | 2/1991 | Löfgren et al. | |
| 5,478,149 A | | 12/1995 | Quigg | |

(Continued)

FOREIGN PATENT DOCUMENTS

| CN | 108176316 A | 6/2018 |
|---|---|---|
| CN | 208260678 U | 12/2018 |

(Continued)

OTHER PUBLICATIONS

Intellectual Property Office of Singapore, Search Report in counterpart Singapore Application No. 10201911111V, dated Aug. 24, 2020.

(Continued)

*Primary Examiner* — David L Sorkin
(74) *Attorney, Agent, or Firm* — Leydig Voit & Mayer, Ltd.

(57) ABSTRACT

An agitator comprising a rotatable impeller comprising blades, magnets, and a shaft, wherein the impeller is configured to be driven by a drive unit magnetically coupled to the impeller, and an impeller seat receiving the rotatable impeller, the impeller seat comprising an upwardly arranged cylindrical housing, a flange, and a base, the cylindrical housing comprising a central opening for the impeller shaft, and the base comprising a collar and pins arranged to engage with a locking and centering mechanism, as well as a mixer engagement unit including the agitator, a mixer system, a mixing vessel, and methods of using the agitator, mixer engagement unit, mixer system, and mixing vessel, are disclosed.

4 Claims, 20 Drawing Sheets

(56) References Cited

U.S. PATENT DOCUMENTS

| | | |
|---|---|---|
| 5,758,965 A | 6/1998 | Gambrill |
| 6,065,865 A * | 5/2000 | Eyraud ............... B01F 13/0872 366/273 |
| 6,382,827 B1 | 5/2002 | Gebrian |
| 6,435,706 B1 | 8/2002 | Bertolotti et al. |
| 6,733,171 B2 | 5/2004 | Schob |
| 6,854,877 B2 | 2/2005 | Hoobyar et al. |
| 7,001,063 B1 | 2/2006 | Markle |
| 7,396,153 B2 | 7/2008 | Andersson |
| 7,513,680 B2 | 4/2009 | Reusche et al. |
| 7,547,135 B2 | 6/2009 | Kocienski |
| 7,629,167 B2 | 12/2009 | Hodge et al. |
| 7,832,922 B2 | 11/2010 | Schoeb |
| 7,874,719 B2 | 1/2011 | Markle et al. |
| 8,128,277 B2 | 3/2012 | Meier |
| 8,226,289 B2 | 7/2012 | Lindeberg |
| 8,684,592 B2 | 4/2014 | Miller et al. |
| 8,783,942 B2 | 7/2014 | Johansson |
| 8,905,728 B2 | 12/2014 | Blankemeier et al. |
| 8,905,729 B2 | 12/2014 | Blankemeier et al. |
| 9,403,135 B2 | 8/2016 | Cutting |
| 9,550,157 B2 | 1/2017 | Erdenberger et al. |
| 9,630,157 B2 | 4/2017 | Li et al. |
| 9,670,448 B2 | 6/2017 | Zeuch et al. |
| 9,873,858 B2 | 1/2018 | Boddenberg et al. |
| 9,956,534 B2 | 5/2018 | Hammerschmidt et al. |
| 2008/0008028 A1* | 1/2008 | Terentiev ............ B01F 13/0032 366/273 |
| 2015/0003189 A1 | 1/2015 | Werth et al. |

FOREIGN PATENT DOCUMENTS

| | | |
|---|---|---|
| EP | 1 470 856 A1 | 10/2004 |
| EP | 1 381 451 B1 | 3/2005 |
| EP | 1 909 951 B1 | 5/2012 |
| EP | 3409985 A1 | 12/2018 |
| KR | 200486653 Y1 | 6/2018 |
| KR | 10-2018-0113270 A | 10/2018 |

OTHER PUBLICATIONS

European Patent Office, Extended European Search Report in counterpart European Application No. 19212617.5, dated May 12, 2020.

* cited by examiner

RADIALLY DRIVEN AGITATOR

BACKGROUND OF THE INVENTION

The preparation of fluids, particularly solutions and suspensions in the pharmaceutical and biopharmaceutical industries, typically involves thorough mixing to provide the desired distribution of ingredients in the product. Many mixing operations are carried out in a vessel with an agitator (e.g., as part of a mixer including an impeller mounted near the base of the vessel), and the agitator is operated to mix the ingredients in the vessel.

However, there is a need for improved agitators.

The present invention provides for ameliorating at least some of the disadvantages of the prior art. These and other advantages of the present invention will be apparent from the description as set forth below.

BRIEF SUMMARY OF THE INVENTION

An embodiment of the invention provides an agitator comprising (a) a rotatable impeller comprising two or more blades, two or more magnets, and a shaft, wherein the impeller is configured to be driven by a drive unit magnetically coupled to the impeller; (b) an impeller seat receiving the rotatable impeller, the impeller seat comprising an upwardly arranged cylindrical housing, a flange, and a base, the cylindrical housing comprising a central opening for the impeller shaft, and the base comprising a collar and at least 3 pins arranged to engage with a locking and centering mechanism.

In another embodiment, a mixer engagement system is provided comprising an embodiment of the agitator, and, (c) a locking and centering mechanism comprising a rotatable hollow cylindrical housing comprising at least 3 angled slots configured to receive the pins of the impeller seat, each slot comprising an open end, a downwardly angled channel, and a closed end; and (d) a lever mounted to the rotatable hollow cylindrical housing, wherein, when the impeller seat is placed in contact with the locking and centering mechanism, with the pins in the open ends of respective slots, and the lever is in a first open position, movement of the lever from the first open position to a second closed position rotates the rotatable cylindrical housing such that the pins move downwardly in the slots along the downwardly angled channels to the closed ends, locking the impeller seat into a fixed and compressed position.

A mixer system according to an embodiment of the invention comprises an embodiment of the mixer engagement system, and, a drive unit comprising a motor and two or more magnets, wherein the drive unit is removably insertable into the rotatable hollow cylindrical housing of the locking and centering mechanism, and once inserted, the drive unit can be operated to magnetically drive the impeller.

In another embodiment, a mixing vessel for use in bioprocessing is provided comprising a biocontainer comprising a closed container having an interior volume suitable for containing fluid, the container comprising a bottom wall having an interior surface and an exterior surface, a top wall, at least one side wall, the side wall(s) being joined to the top wall and the bottom wall; and at least one inlet port, and at least one drain port, the drain port being arranged in the bottom wall; and, an embodiment of the agitator, wherein the flange is mounted to the interior surface of the bottom wall.

An embodiment of a method for processing fluid according to the invention comprises placing a mixing vessel for use in bioprocessing comprising a biocontainer comprising a closed container having an interior volume suitable for containing fluid, the container comprising a bottom wall having an interior surface and an exterior surface, a top wall, at least one side wall, the at least one side wall being joined to the top wall and the bottom wall; and at least one inlet port, and at least one drain port, the drain port being arranged in the bottom wall; and, an embodiment of the agitator, wherein the flange is mounted to the interior surface of the bottom wall, in a tote; engaging an embodiment of the locking and centering mechanism with the impeller seat and moving the lever from the first open position to the second closed position, and inserting the drive unit into the rotatable hollow cylindrical housing of the locking and centering mechanism until the magnets in the drive unit are aligned with the magnets in the impeller.

BRIEF DESCRIPTION OF THE SEVERAL VIEWS OF THE DRAWING(S)

Figure 3A:
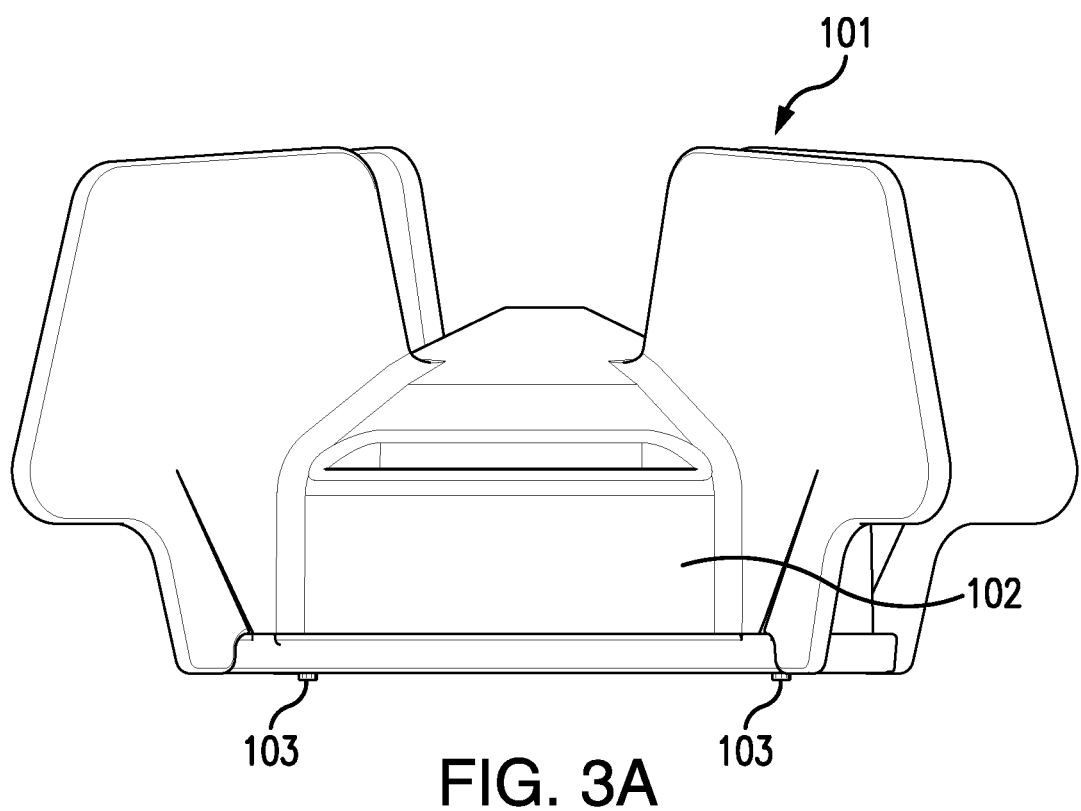
Figure 3B:
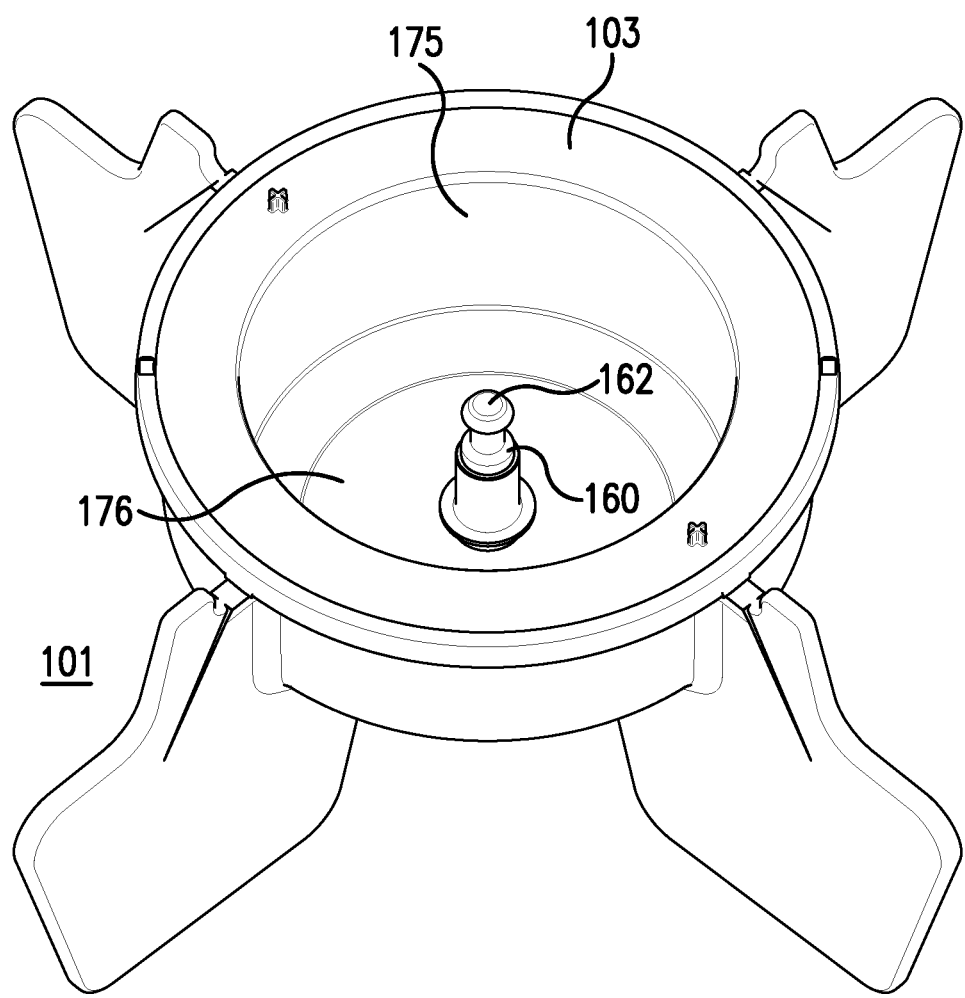
Figure 3C:
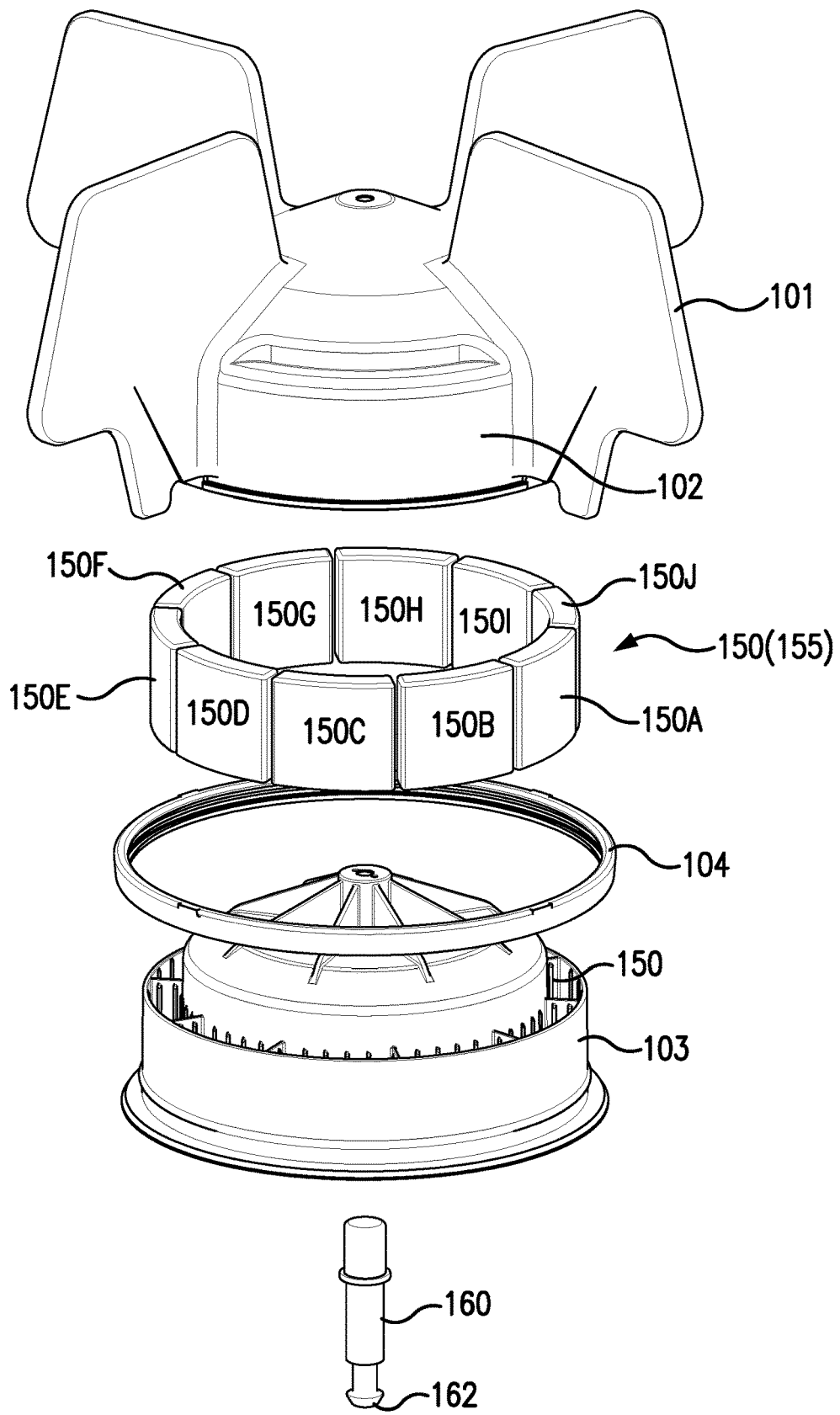

FIG. 3A shows a side view; FIG. 3B shows a bottom perspective view; and FIG. 3C shows an exploded view, of a rotatable impeller according to an embodiment of the invention. The exploded view also shows an array of driven magnets in the impeller.

Figure 4A:
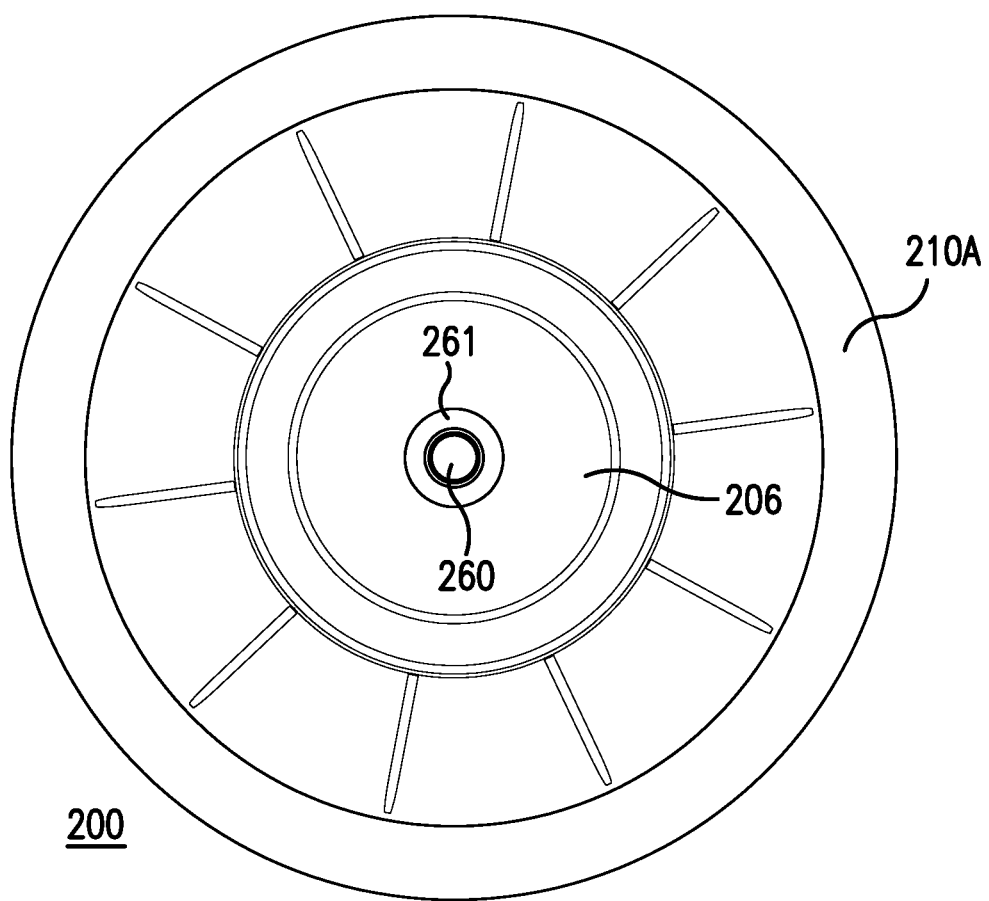
Figure 4B:
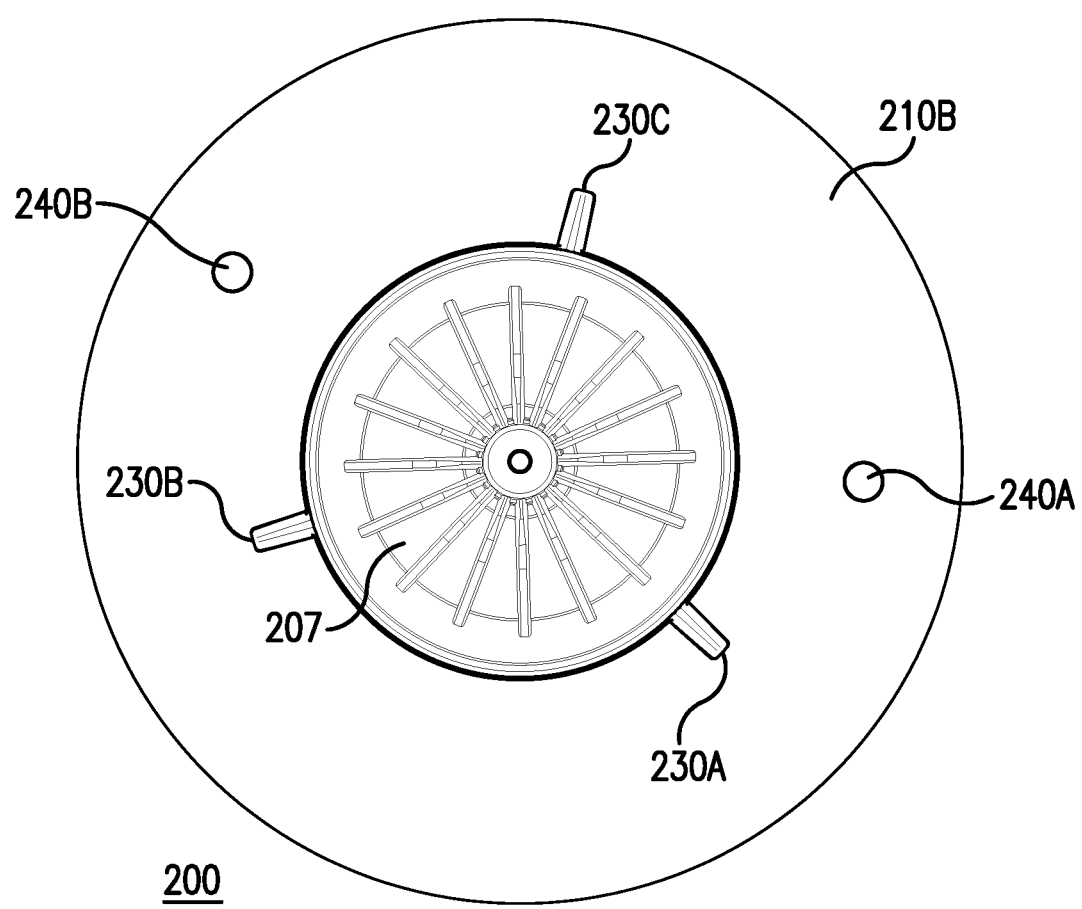
Figure 4C:
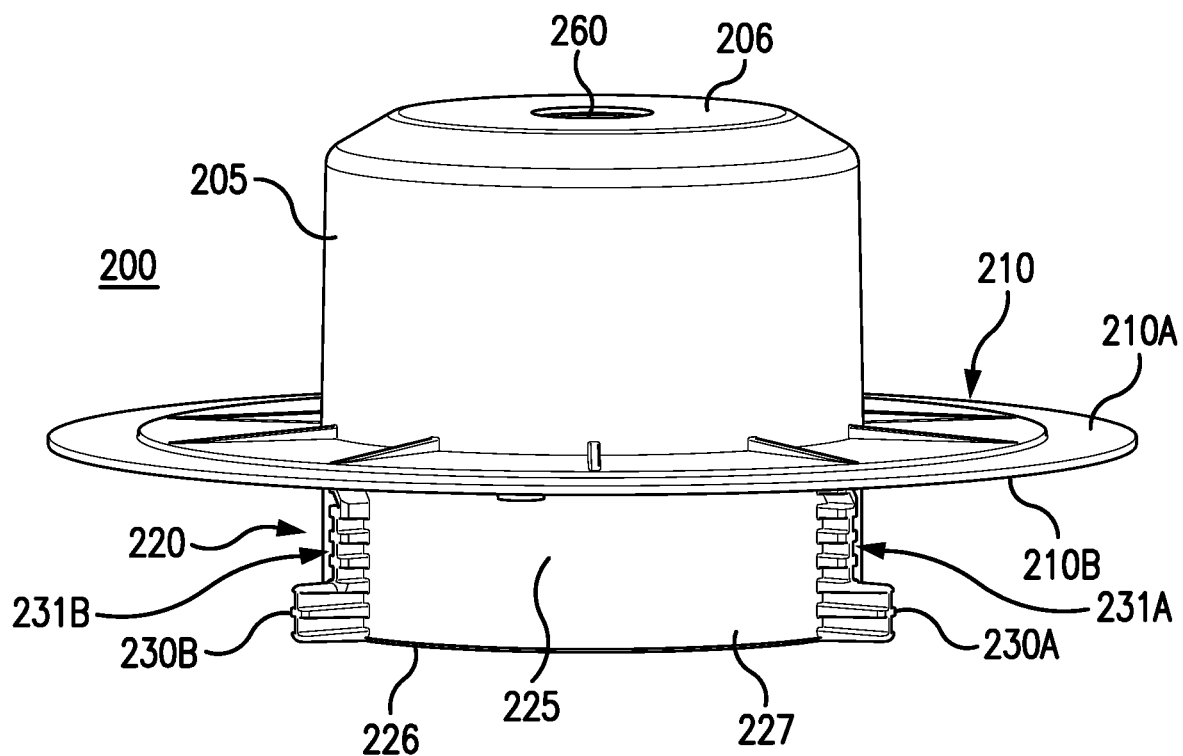

FIG. 4A shows a top view; FIG. 4B shows a bottom view; and FIG. 4C shows a side view, of an impeller seat according to an embodiment of the invention.

Figure 5:
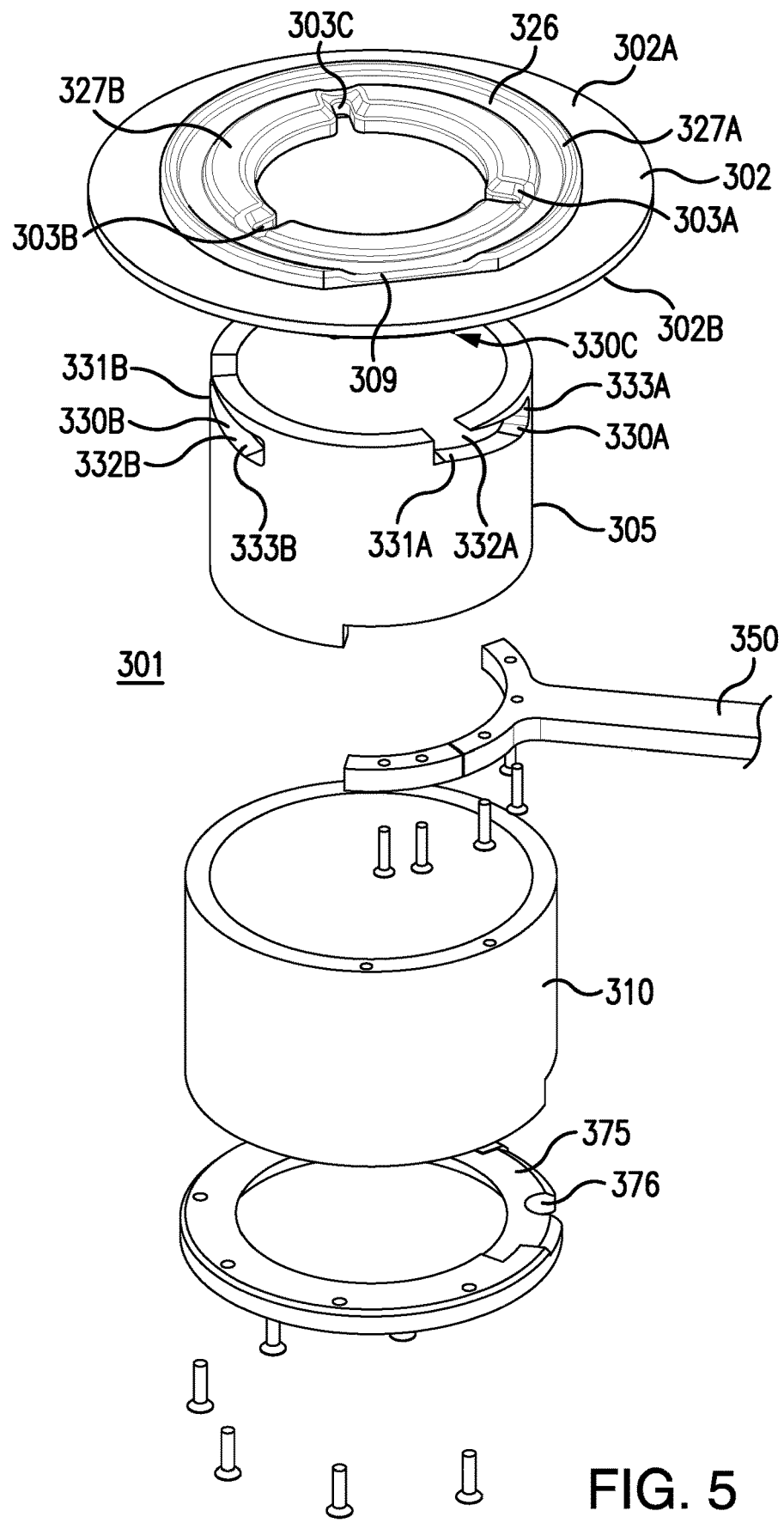

FIG. 5 shows an exploded view of a locking and centering mechanism according to an embodiment of the invention.

Figure 6:
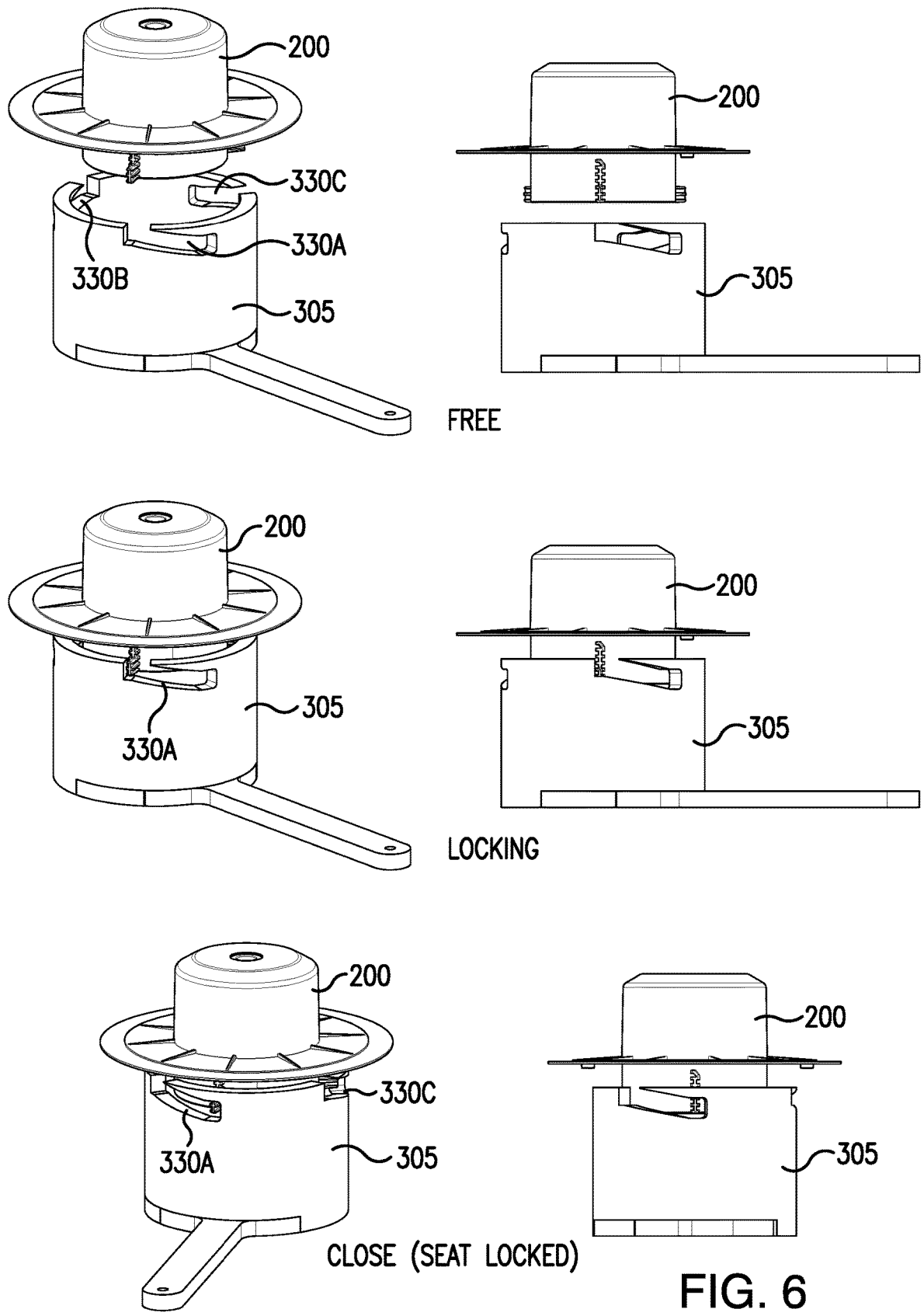

FIG. 6 shows, diagrammatically, in perspective and side views, the impeller seat and the locking and centering mechanism shown in FIGS. 4A-4C and 5 (without the face plate and shell shown in FIG. 5), placed in contact with each other, wherein the impeller seat is in the open position in the middle view, and in the locked position in the right hand view.

Figure 7A:
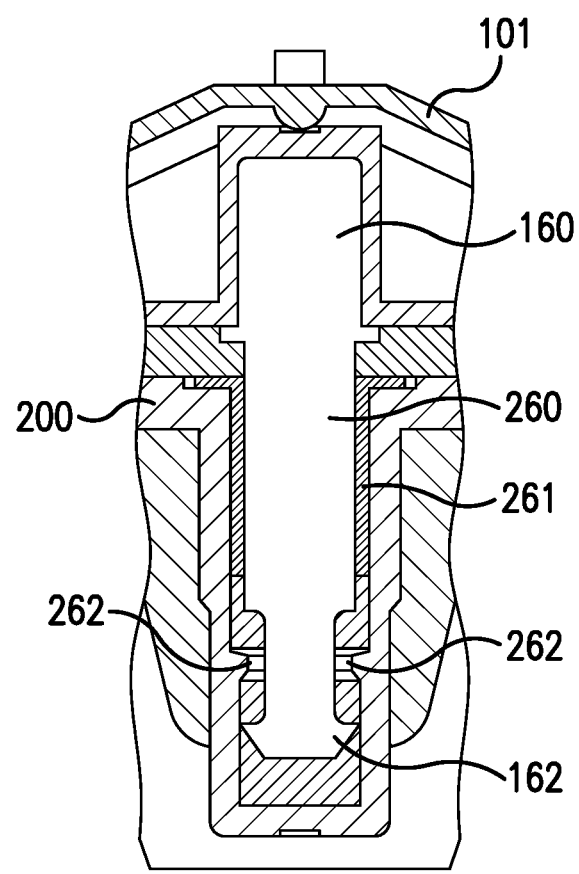
Figure 7B:
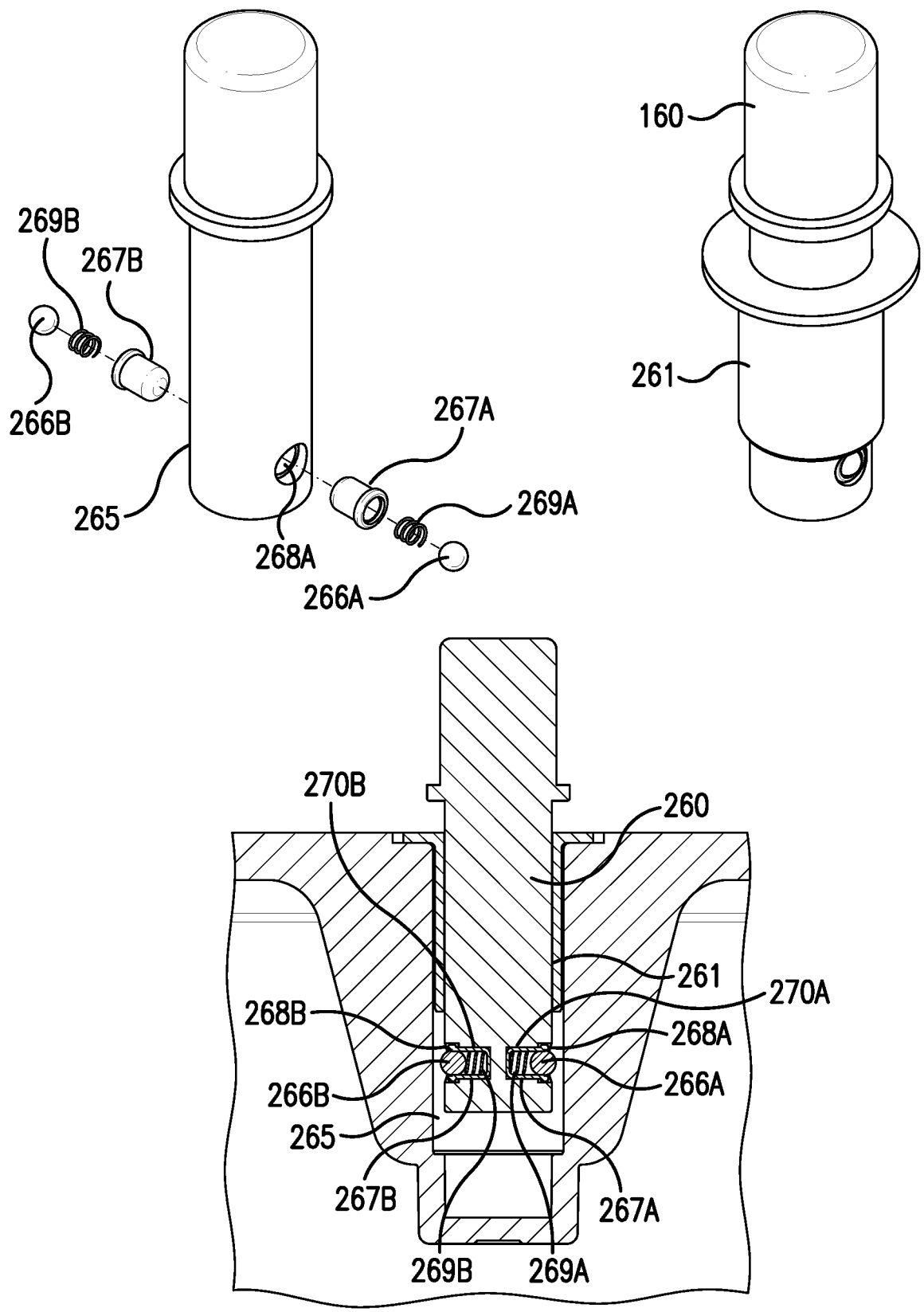

FIG. 7A shows, in partial cross-sectional view, the rotatable impeller engaged with the impeller seat according to an embodiment of the invention, wherein the end of the impeller shaft has passed through a shoulder in the central opening of the impeller seat. FIG. 7B shows, in partial cross-sectional view, and in perspective views (with and without a bearing), another arrangement for engaging the rotatable impeller with the impeller seat according to another embodiment of the invention, comprising a spring-loaded ball pressed into the shaft, wherein the central opening of the lacks a shoulder.

Figure 8A:
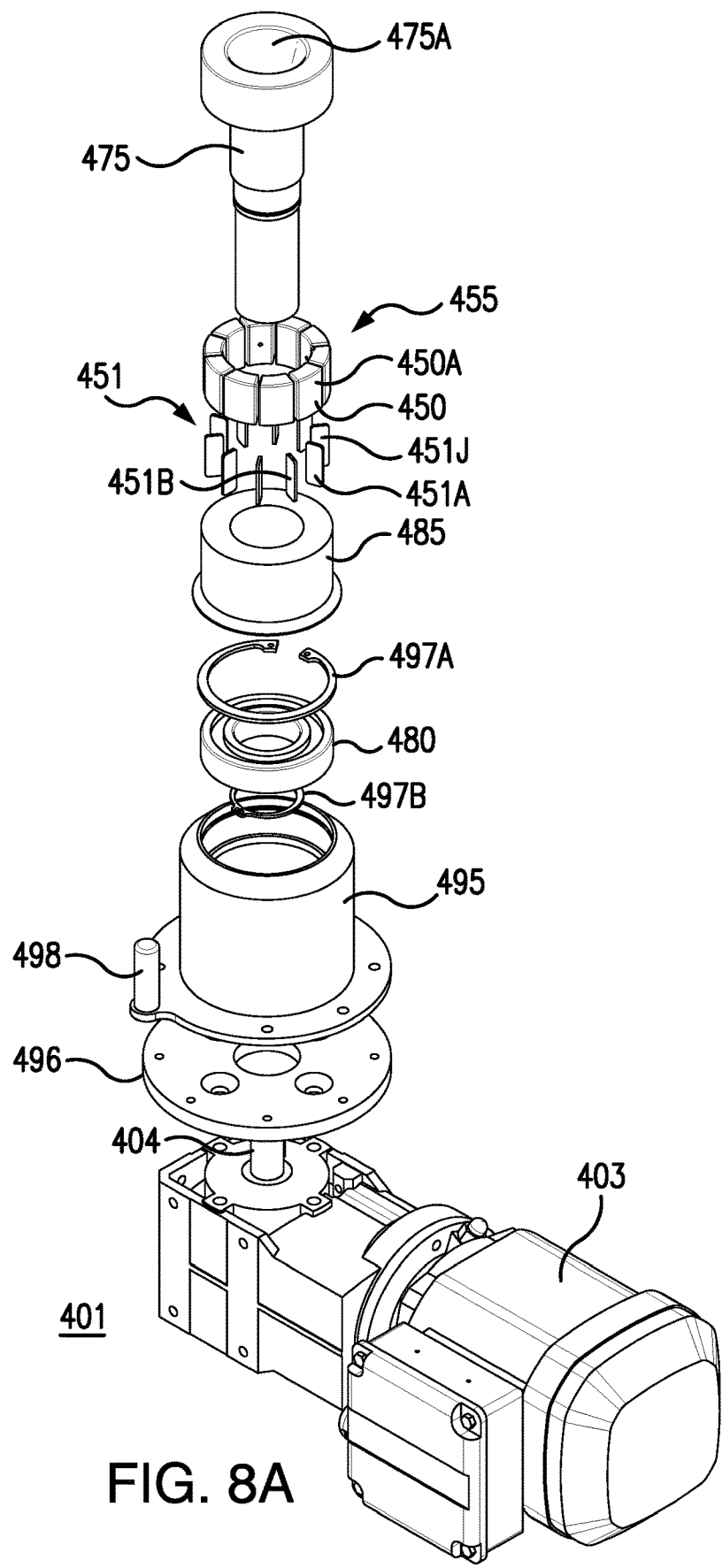
Figure 8B:
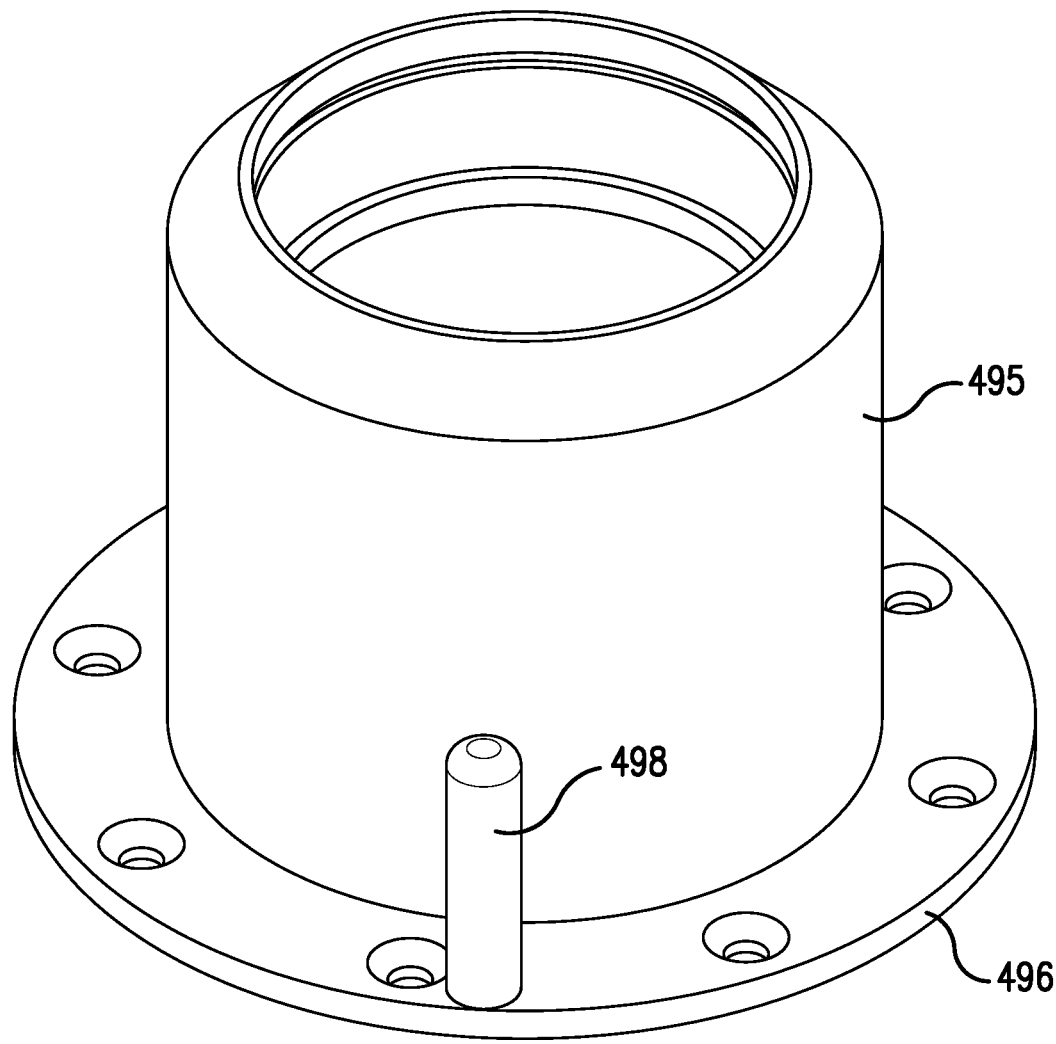

FIG. 8A shows an exploded view of a drive unit according to an embodiment of the invention, also showing an array of drive magnets; FIG. 8B shows a drive unit shaft housing, a base plate, and an upwardly facing post.

Figure 9A:
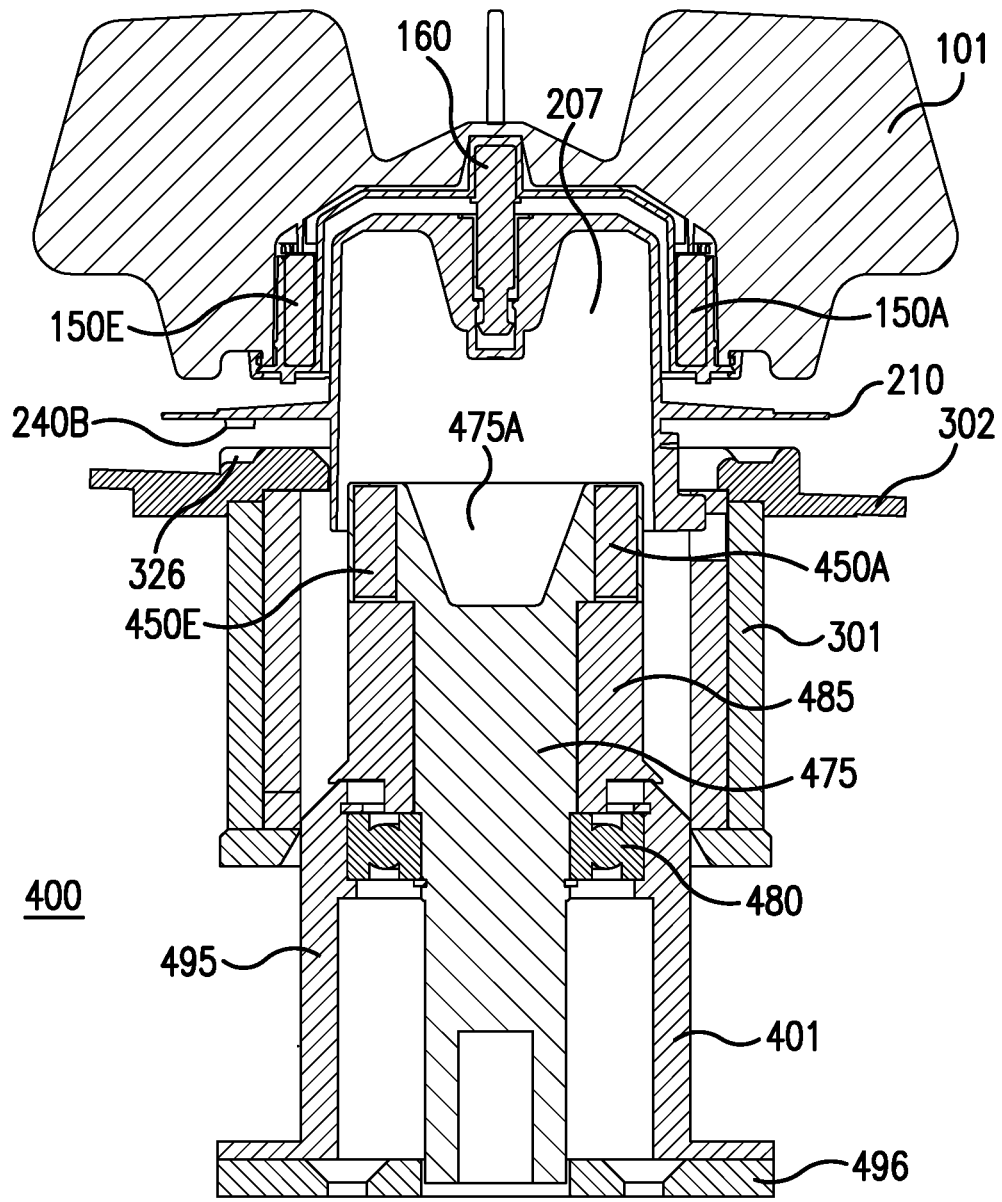
Figure 9B:
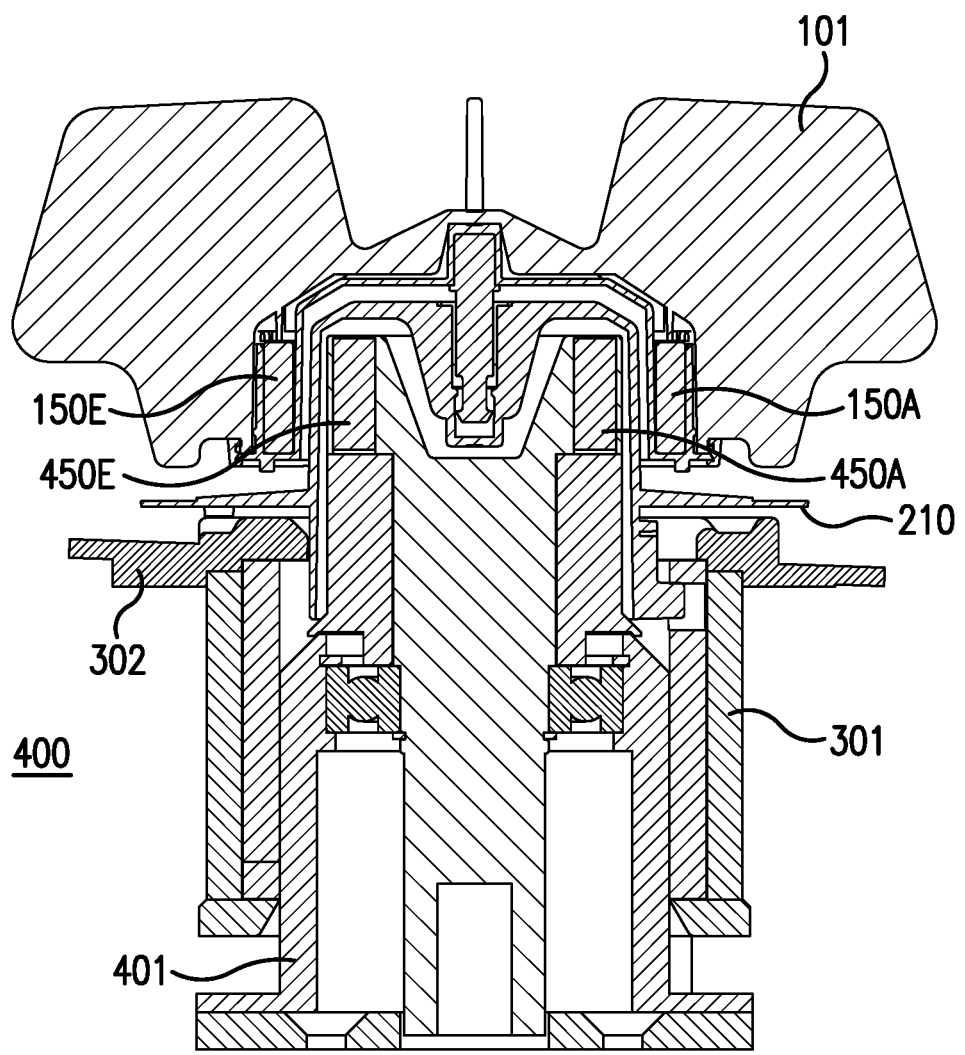

FIG. 9 shows, in diagrammatic side views, insertion of the removable drive unit into an embodiment of the mixer engagement system, wherein FIG. 9A shows partial insertion, and FIG. 9B shows full insertion.

Figure 10:
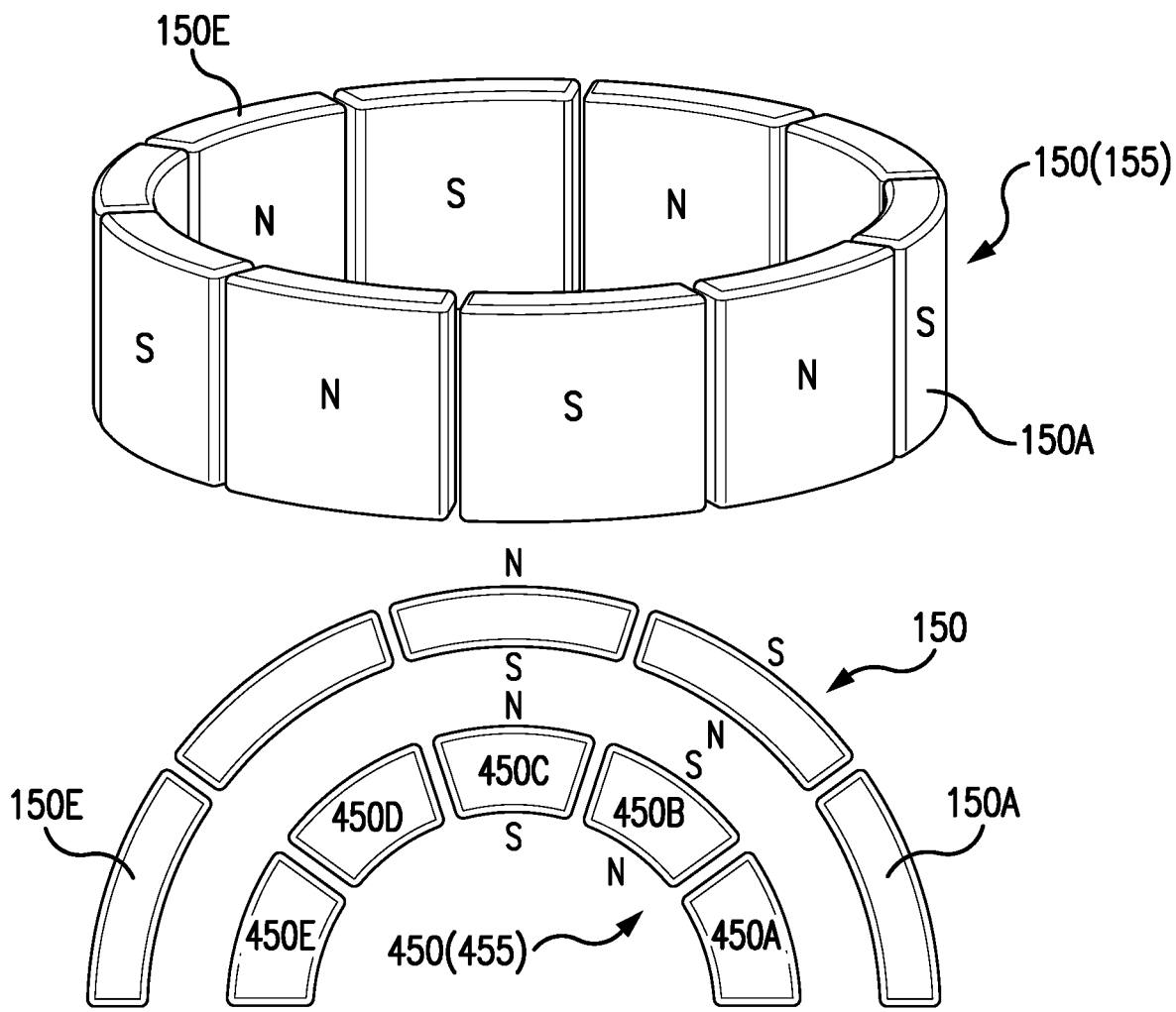

FIG. 10 shows a partial view of magnets in the impeller and the drive unit arranged with opposite polarities after full insertion of the drive unit as shown in FIG. 9B.

Figure 11:
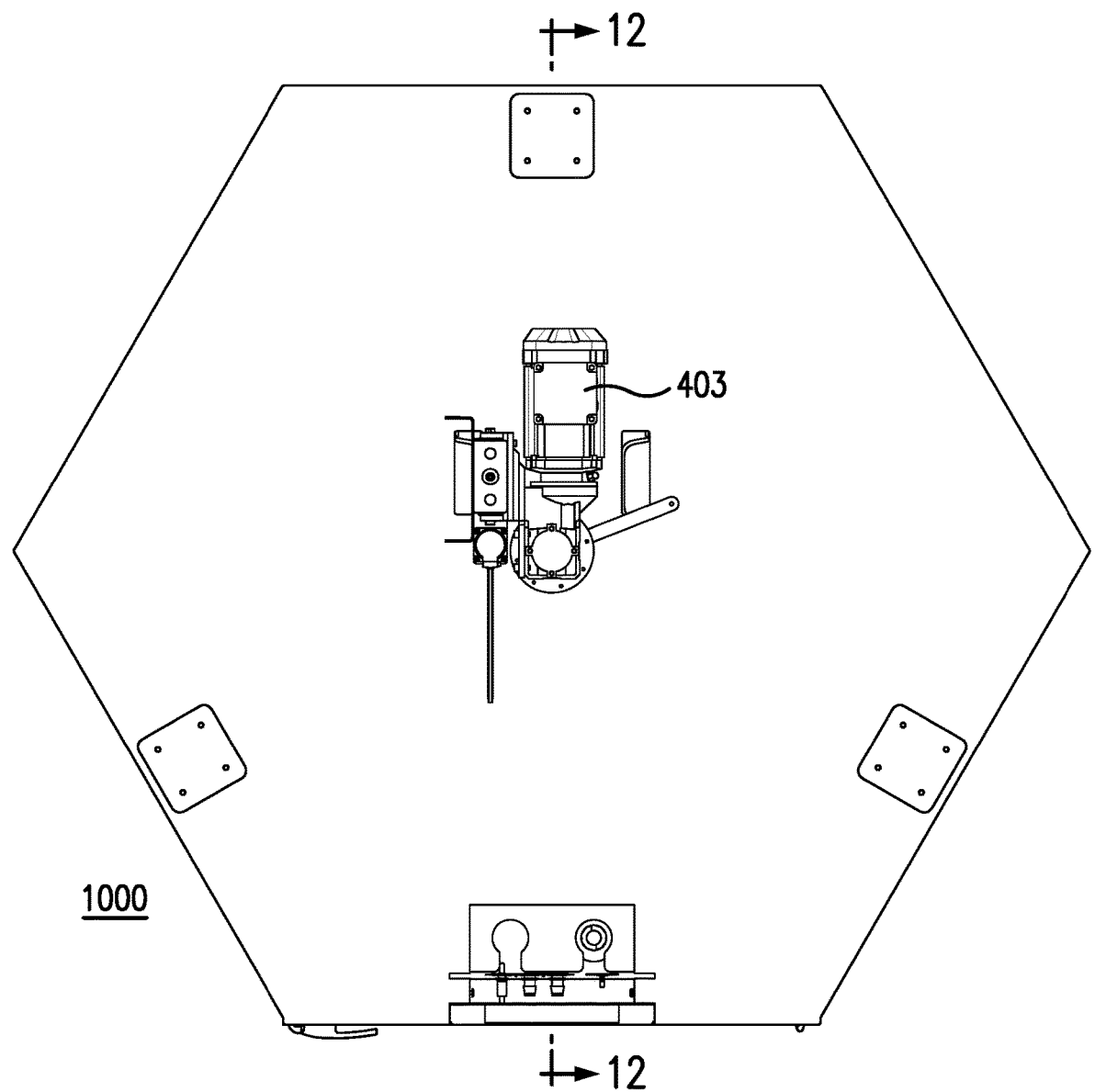
Figure 12:
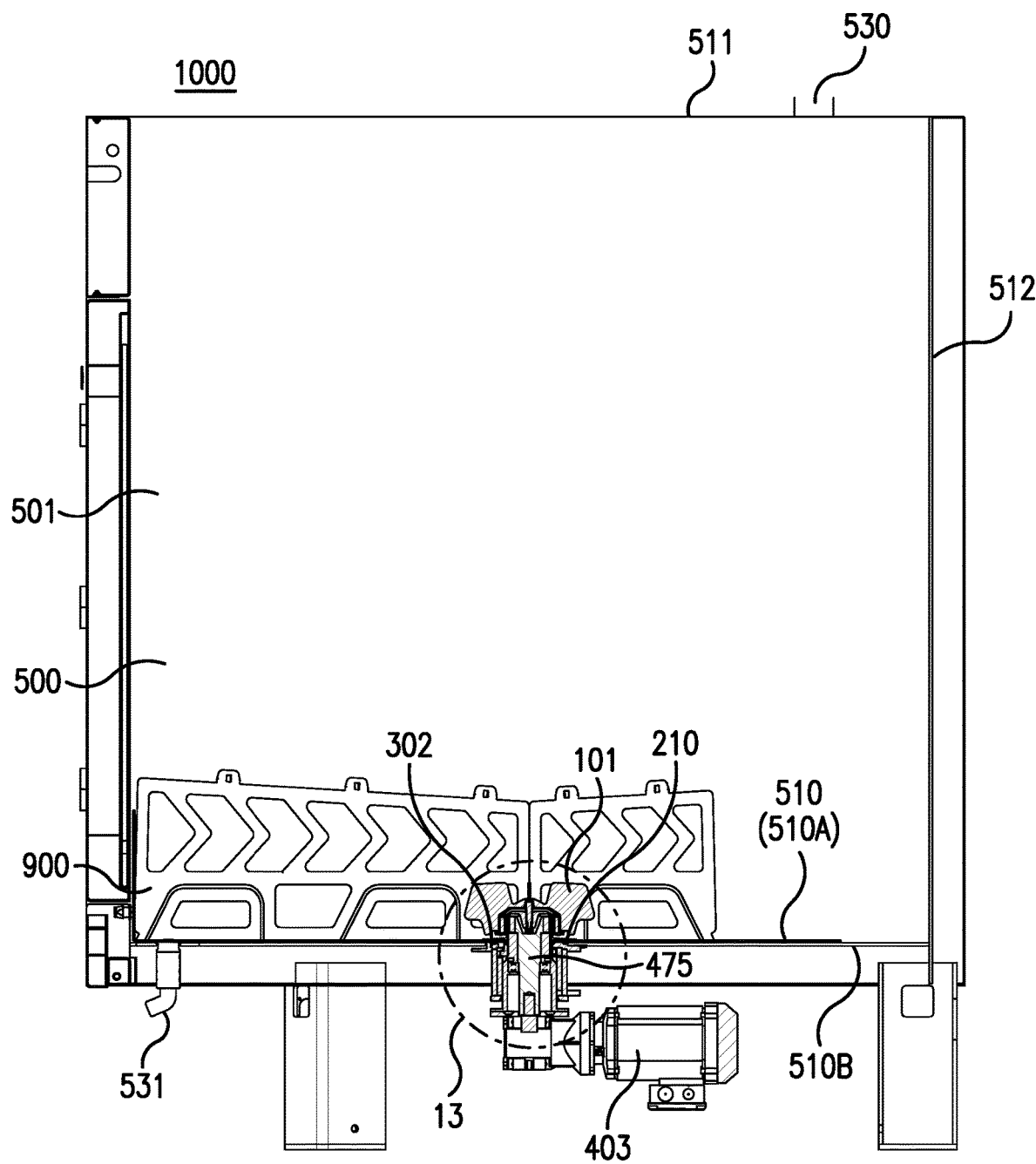
Figure 13:
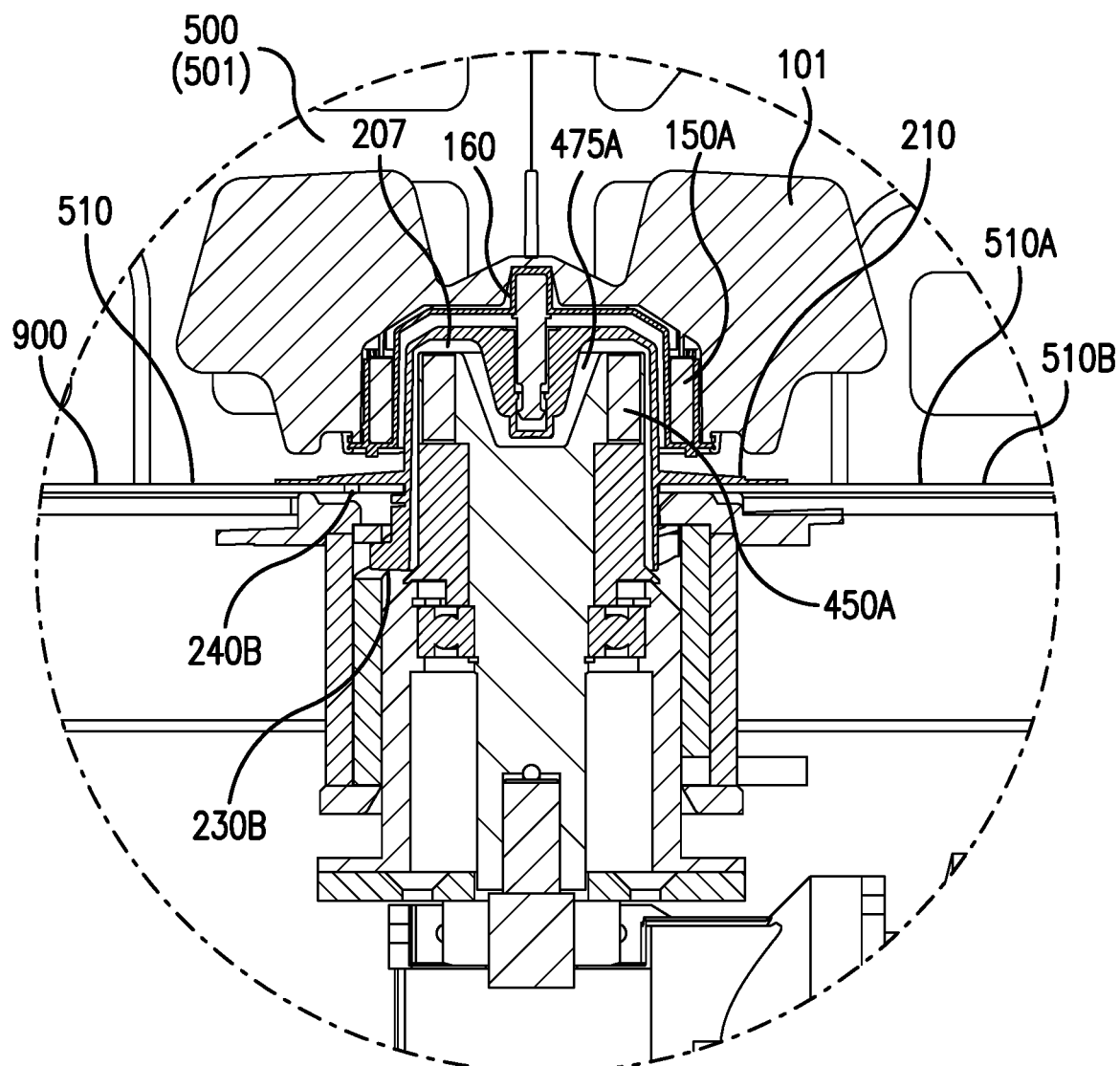

FIGS. 11-13 show an illustrative tote for receiving a missing vessel, also showing a motor of the drive unit. FIG. 11 shows a bottom view of the tote, FIG. 12 shows a cross-sectional view of the tote with mixing vessel along line 12-12 of FIG. 11, and FIG. 13 shows a partial detail view of FIG. 12.

DETAILED DESCRIPTION OF THE INVENTION

In accordance with an embodiment of the invention, an agitator is provided comprising (a) a rotatable impeller comprising two or more blades, two or more magnets, and a shaft, wherein the impeller is configured to be driven by a drive unit magnetically coupled to the impeller; (b) an impeller seat receiving the rotatable impeller, the impeller seat comprising an upwardly arranged cylindrical housing, a flange, and a base, the cylindrical housing comprising a central opening for the impeller shaft, and the base comprising a collar and at least 3 pins arranged to engage with a locking and centering mechanism.

In another embodiment, a mixer engagement system is provided comprising an embodiment of the agitator, and, (c) a locking and centering mechanism comprising a rotatable hollow cylindrical housing comprising at least 3 angled slots configured to receive the pins of the impeller seat, each slot comprising an open end, a downwardly angled channel, and a closed end; and (d) a lever mounted to the rotatable hollow cylindrical housing, wherein, when the impeller seat is placed in contact with the rotatable locking and centering mechanism, with the pins in the open ends of respective slots, and the lever is in a first open position, movement of the lever from the first open position to a second closed position rotates the rotatable hollow cylinder housing such that the pins move downwardly in the slots along the downwardly angled channels to the closed ends, locking the impeller seat into a fixed and compressed position.

A mixer system according to an embodiment of the invention comprises an embodiment of the mixer engagement system, and, a drive unit comprising a motor and two or more magnets, wherein the drive unit is removably insertable into the rotatable hollow cylindrical housing of the locking and centering mechanism, and once inserted, the drive unit can be operated to magnetically drive the impeller.

In another embodiment, a mixing vessel for use in bioprocessing is provided comprising a biocontainer comprising a closed container having an interior volume suitable for containing fluid, the container comprising a bottom wall having an interior surface and an exterior surface, a top wall, at least one side wall, the side wall(s) being joined to the top wall and the bottom wall; and at least one inlet port, and at least one drain port, the at least one drain port being arranged in the bottom wall; and, an embodiment of the agitator, wherein the flange is mounted to the interior surface of the bottom wall.

An embodiment of a method for processing fluid according to the invention comprises placing a mixing vessel for use in bioprocessing comprising a biocontainer comprising a closed container having an interior volume suitable for containing fluid, the container comprising a bottom wall having an interior surface and an exterior surface, a top wall, at least one side wall, the at least one side wall being joined to the top wall and the bottom wall; and at least one inlet port, and at least one drain port, the at least one drain port being arranged in the bottom wall; and, an embodiment of the agitator, wherein the flange is mounted to the interior surface of the bottom wall, in a tote; engaging an embodiment of the locking and centering mechanism with the impeller seat and moving the lever from the first open position to the second closed position, and inserting the drive unit into the rotatable hollow cylindrical housing of the locking and centering mechanism until the magnets in the drive unit are aligned with the magnets in the impeller. A typical embodiment of the method further comprises introducing at least one fluid into the container, operating the drive unit to magnetically drive the impeller and mix material in the container, and subsequently draining the mixed material from the container.

Illustratively, an embodiment of a method for processing fluid comprises (A) obtaining a biocontainer comprising a closed container having an interior volume suitable for containing fluid, the container comprising a bottom wall having an interior surface and an exterior surface, a top wall, at least one side wall, the side wall(s) being joined to the top wall and the bottom wall; and at least one inlet port, and at least drain port, the at least one drain port being arranged in the bottom wall; and, a mixing engagement system comprising an agitator comprising (a) a rotatable impeller comprising two or more blades, two or more magnets, and a shaft, wherein the impeller is configured to be driven by a drive unit magnetically coupled to the impeller; (b) an impeller seat receiving the rotatable impeller, the impeller seat comprising an upwardly arranged cylindrical housing, a flange, and a base, the cylindrical housing comprising a central opening for the impeller shaft, and the base comprising a collar and at least 3 pins arranged to engage with a locking and centering mechanism, wherein the flange is mounted to the interior surface of the bottom wall of the container; and, (c) a locking and centering mechanism comprising a rotatable hollow cylindrical housing comprising at least 3 angled slots configured to receive the pins of the impeller seat, each slot comprising an open end, a downwardly angled channel, and a closed end; and (d) a lever mounted to the rotatable hollow cylindrical housing, wherein, when the impeller seat is placed in contact with the locking and centering mechanism, with the pins in the open ends of respective slots, and the lever is in a first open position, movement of the lever from the first open position to a second closed position rotates the rotatable hollow cylindrical housing such that the pins move downwardly in the slots along the downwardly angled channels to the closed ends, locking the impeller seat into a fixed and compressed position; (B) moving the lever from the first open position to the second closed position and engaging the impeller seat with the locking and centering mechanism; (C) inserting a removable drive unit comprising a motor and two or more magnets into the rotatable hollow cylindrical housing of the locking and centering mechanism, and, once the biocontainer contains fluid to be processed, operating the drive unit to magnetically drive the impeller and mix the fluid in the biocontainer.

Since the mixing vessel is for single use, after mixing (and before or after draining), the drive unit is removed and the lever is moved from the second closed position to the first open position, and the mixing vessel is discarded. The mixer engagement system and drive unit and be re-used with other mixing vessels.

Advantageously, radially driven mixers can be provided that can be upscaled to mix large volumes and/or a higher speeds, and provide improved performance. A variety of different drive units can be produced by selecting the magnet dimensions, magnet strength, and the amount of magnets used. For example, a torque of about 19 Nm, or more, can be achieved.

Moreover, the shaft of the drive unit can be centered (aligned on the same rotation axis of the impeller) and the seat can be locked into a fixed and compressed position. Thus, the magnets in the drive unit (wherein the drive unit is removable) and in the impeller can be well aligned with each other while not having any contact with any of the parts in between, and the impeller seat (where the impeller is attached) is fixed to the container (bag) such that the seat does not wobble during operation. Thus, the impeller does not touch the seat during mixing, and the impeller shaft does not touch the inside of the seat. In effect, tolerances can be reduced to essentially zero. The removable drive unit can be used with a variety of other containers and systems. "Removable" in this context means that the drive unit can be operated so that magnet holder shaft can move up into the impeller seat and down out of the impeller seat. It should be understood that the drive unit can be a fixed drive unit on the tank, or mounted on a trolley such that the drive unit can be removed from the tank and moved on the trolley for use with another tank.

Each of the components of the invention will now be described in more detail below, wherein like components have like reference numbers.

FIGS. 1, 2, and 3A-3C illustrate an embodiment of an agitator 100 comprising a rotatable impeller 101 comprising two or more blades 110, (4 are shown, labeled as 110A, 110B, 110C, and 110D), at least two permanent driven magnets 150 (labeled as 150A-150J in FIG. 3C); preferably, a plurality of magnets are arranged with alternating polarities, in a circular configuration as shown in FIG. 10), an interior surface 175 defining a cavity 176, and a shaft 160, wherein the impeller is configured to be driven by a drive unit magnetically coupled to the impeller. If desired, the impeller can be produced by, for example, injection moulding, e.g., including an upper part 102 (e.g., in which the shaft is injection moulded) and a lower part 103 (in which the magnets are inserted) and the top and bottom parts are assembled and sealed with a plastic ring overmould 104. If desired, impellers can be produced with different shaped and/or sized blades in the top part, wherein the same bottom part can be used with different top parts.

The illustrated embodiment of the agitator also includes an impeller seat 200 (as shown in more detail in FIGS. 4A-4C) for receiving the rotatable impeller 101, the impeller seat comprising an upwardly arranged cylindrical housing 205 comprising an interior cavity 207, a top end 206 including a central opening 260 including a bearing 261 having an inner diameter for receiving the impeller shaft, a flange 210 having an upper surface 210A and a lower surface 210B, and a base 220, the base comprising a collar 225 having a lower end 226 and a side wall 227 and at least 3 pins 230A, 230B, and 230C arranged to engage with a locking and centering mechanism. As will be discussed in more detail below, arranged above, and aligned with, each pin, is an anti-rotation tab that will fit in a notch in the face plate 302 of the locking and centering mechanism 301. FIG. 4C shows anti-rotation tabs 231A and 231B, arranged above, and aligned with, pins 230A and 230B, respectively (anti-rotation tab 231C, arranged above, and aligned with, pin 230C, not shown). FIG. 4C also shows that the tabs have a length extending from the collar that is less than the length of the pins. Typically, the lower surface 210B includes at least one stub for positioning during the container (bag) manufacturing process. In this illustrated embodiment, the lower surface includes 2 stubs 240A, 240B.

In some embodiments (e.g., as shown in FIGS. 12 and 13), the stubs fit into openings in a support (sometimes referred to as tray, folder, or rigid base) used for carrying a biocontainer comprising the impeller, or fit into a radial groove of the face plate when a support is not used. A variety of supports can be used in accordance with embodiments of the invention, e.g., as described in U.S. Pat. No. 9,687,852.

Optionally, as shown in FIG. 7A, the central opening 260 includes a shoulder 262 on the lower part of the surface of the opening, located below the bearing 261, and the impeller shaft 160 includes an enlarged end 162, such that the end of the shaft, passing through the shoulder 262 is retained in the opening 260 once the impeller is inserted into the seat, preventing the impeller from coming out of the seat during transport of a biocontainer containing the agitator.

Alternatively, in another option, the central opening does not include a shoulder, and the impeller shaft does not include an enlarged end. For example, the shaft can include a spring-loaded mount, for example, including at least one spring-loaded ball retained in the shaft. The spring-loaded ball can be fitted into a retaining sleeve that is in turn fitted, for example, press-fitted or screwed, into a bore in the shaft.

In accordance with the embodiment shown in FIG. 7B, the shaft 160 includes a spring-loaded mount 265 (insertable into bearing 261), illustrated as spring loaded balls 266A, 266B, with corresponding springs 269A, 269B, fitted into corresponding retaining sleeves 267A, 267B (illustrated with blind ends 270A, 270B) that are in turn press-fit into corresponding bores 268A, 268B in the shaft. In accordance with embodiments including a spring-loaded mount, the bearing 261 presents a barrier that the spring-loaded ball(s) cannot easily pass. While FIG. 7B illustrates a spring loaded mount 265 with two spring loaded balls with corresponding sleeves fit into corresponding bores, in another embodiment, the mount comprises a single spring loaded ball and a corresponding retaining sleeve fit into a bore.

FIGS. 1, 2, 5, and 6 illustrate an embodiment of a mixer engagement system 300 comprising an embodiment of the agitator 100, and a locking and centering mechanism 301 comprising a face plate 302 having a top surface 302A and a bottom surface 302B, and including at least 3 notches 303A, 303B, 303C (face plate not shown in FIG. 6 for ease of viewing), the face plate being mounted to a hollow shell or hollow outer housing 310, and a rotatable hollow cylindrical inner housing 305 arranged within the shell 310 (shell also not shown in FIG. 6 for ease of viewing), the housing 305 including at least 3 downwardly angled slots 330A, 330B, 330C configured to communicate with the notches of the face plate and receive the pins and anti-rotation tabs of the impeller seat, each slot respectively comprising an open end (331A, 331B, 331C), a downwardly angled channel (332A, 332B, 332C), and a closed end (333A, 333B, 333C); and a lever 350 mounted to the hollow cylindrical housing 305, wherein, when the impeller seat is placed in contact with the locking and centering mechanism, with the pins through the notches and in the open ends of respective slots, and the lever is in a first open position (middle view FIG. 6), movement of the lever (mounted to the rotatable housing 305, the housing 305 rotating within the non-rotating shell 310) from the first open position to a second closed position (right hand view FIG. 6) rotates the housing 305 such that the pins move downwardly in the slots along the downwardly angled channels to the closed ends, locking the impeller seat into a fixed and compressed position. In some embodiments, as shown in FIGS. 5, 12, and 13, the top surface 302A of the face plate includes a radial groove 326 (between upraised portions 327A and 327B) configured to receive the stubs 240A, 240B (e.g., wherein a support for carrying a biocontainer comprising the impeller is not used). FIG. 5 shows the lever 350 attached to the housing 305, and the base plate 376 attached to the shell 310, by pins or screws, but other arrangements for attachment are known to one of skill in the art.

Using FIGS. 4B, 4C and 5 for reference, the notches 303A, 303B, 303C respectively receive the pins 230A, 230B, and 230C, as well as the anti-rotation tabs 231A, 231B, and 231C. The anti-rotation tabs remain in the notches during the locking process so that the seat is prevented from rotating during the locking process. However, the pins, that are located sufficiently downwardly from the tabs, extend below the bottom surface 302B of the face plate, and are thus able to move downwardly in the slots.

Using FIG. 4C for reference, in those embodiments wherein a support is used (see also, support 900 in FIGS. 12 and 13), the space between the top of the pins 230A, 230B, and 230C and the lower surface 210B allows the support to be placed between the bottom of the biocontainer and the top surface 302A of the face plate 302 of the locking and centering mechanism 301, wherein the stubs 240A and 240B fit in corresponding holes in the support 900. Once the pins are received and moved downwardly into the downwardly angled channels, the seat 200 is prevented from coming out of the support. If desired, as shown in FIG. 5, upraised portion 327A includes a cutout 309, to ensure that the cutout slots are aligned with the pins of the seat, and components are installed and welded in one direction, e.g., to make tank production foolproof.

FIGS. 9A and 9B illustrate an embodiment of a mixer system 400 comprising an embodiment of the engagement system, and, a drive unit 401 (as shown in more detail in FIG. 8A) comprising a motor 403 with a driveshaft 404, a magnet holder shaft 475 having a cavity 475A at the upper end, and at least two permanent drive magnets 450 (labeled as 450A, 450B; preferably, a plurality of magnets are arranged in a circular configuration with alternating polarities (as shown in FIG. 10), that can be separated by a spacer arrangement 851 comprising individual spacers (spacers 451A, 451B, and 451J are labeled); at least one bearing 480, and a shaft housing 495. Typically, and as shown in FIGS. 8A and 8B, the drive unit also includes a base plate 496, and at least one retainer 497, such as a circlip (two retainers are shown, 497A, 497B). The drive unit can also include a magnet cover 485.

Typically, the bearing 480 is pressed on the shaft housing 495, the retainer 497A is mounted above the bearing in the shaft housing, the magnet cover 485 is slid over the shaft of the magnet holder shaft (the magnet holder shaft having the magnets 450 mounted thereon), the magnet holder with installed magnets and mounted magnet cover is pressed on the bearing, another retainer 497B is mounted below the bearing onto the shaft of the magnet holder shaft, the base plate 496 is mounted on the motor 403, and the whole assembly is mounted onto the brace plate.

Figure 1:
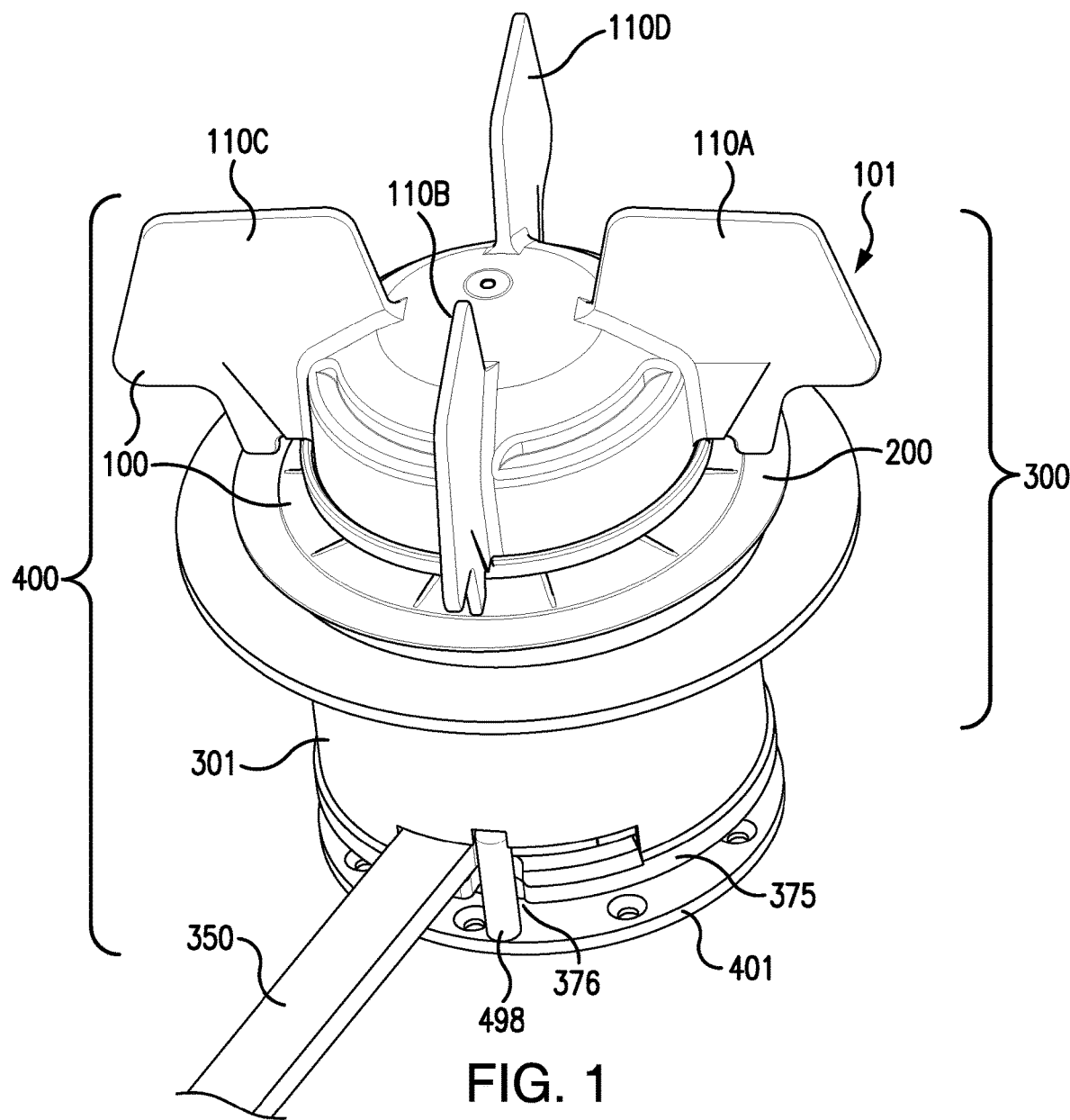
FIG. 1 is perspective view of mixer engagement system according to an embodiment of the invention, showing an agitator comprising a rotatable impeller and an impeller seat receiving the rotatable impeller, and a locking and centering mechanism.
Figure 2:
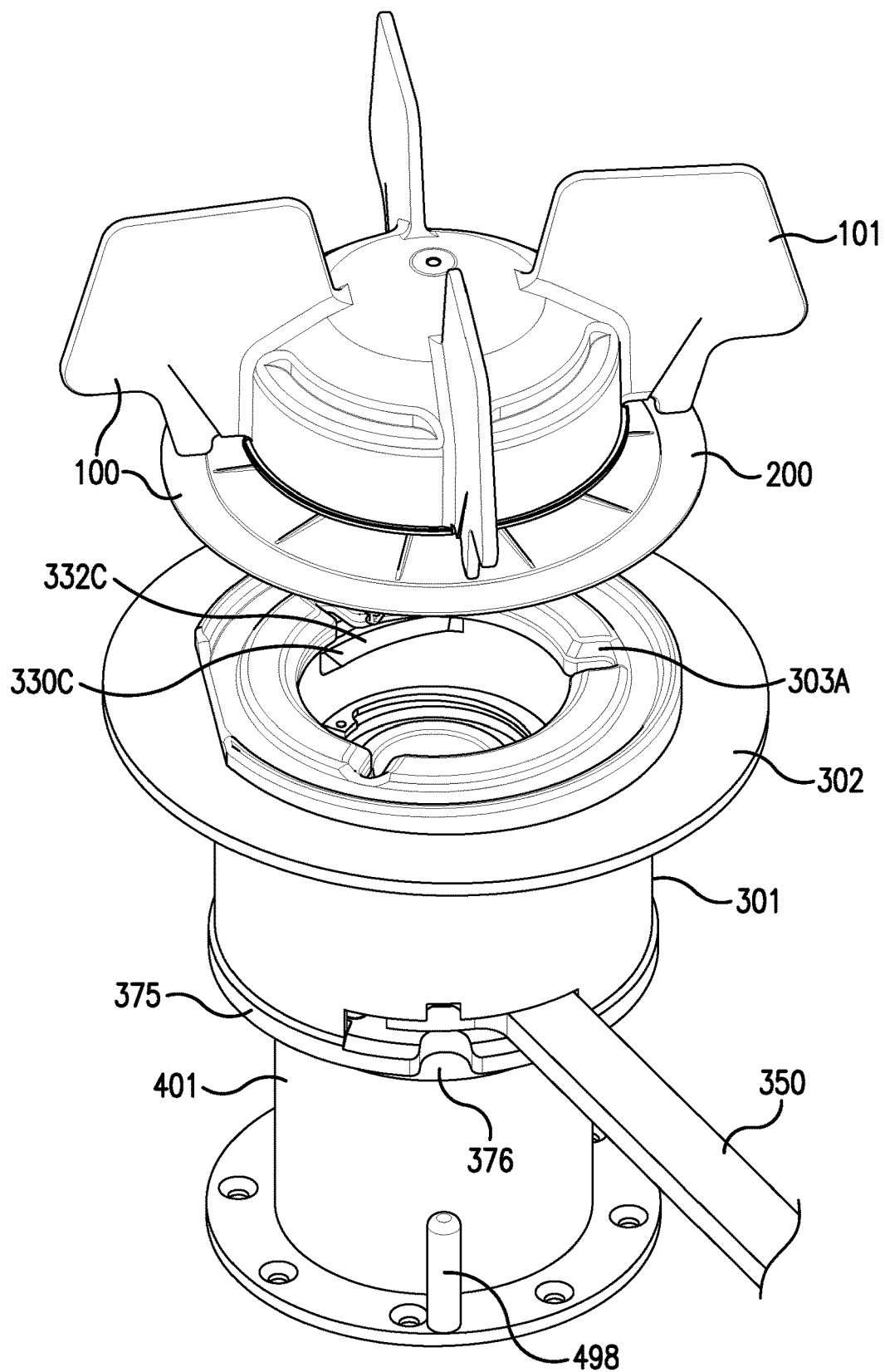
FIG. 2 is an exploded view of the mixer engagement system show in FIG. 1, also showing a base of a drive unit that is removably insertable into the locking and centering mechanism, the mixer engagement system and drive unit providing a mixer system according to another embodiment of the invention.

As shown in FIGS. 9A and 9B, the drive unit is removably insertable into the hollow cylindrical housing 305 of the locking and centering mechanism 301, such that the magnet end of the magnet holder shaft 475 is inserted into interior cavity 207 of the cylindrical housing 205 of the impeller seat 200, and the drive unit can be operated to magnetically drive the impeller. Optionally, as shown in FIGS. 1, 2, and 8B, the base plate includes a safety mechanism comprising an upwardly facing post 498 that can fit in an optional groove 376 in the base plate 375 of the locking and centering mechanism 301, so that when the drive unit is fully inserted, the lever is blocked so that the operator cannot disengage the locking and centering mechanism with the drive unit installed or during operation. In another option (not shown) the post is moved more to the outside without a groove, lever will still be blocked when the drive unit is fully inserted.

As shown in FIGS. 3C and 8A, the impeller 101 and the drive unit 401 each include a magnet array 155, 455, respectively comprising a plurality of permanent magnets 150, 450 (e.g., block magnets, multipole ring magnets, or more preferably, segment magnets) each arranged in a circular format with alternating polarities (wherein the drive magnets are separated by spacers), and facing each other with opposite polarities, e.g., the south pole of an impeller magnet faces the north pole of a drive unit magnet, and the north pole side of an impeller magnet faces the south pole of a drive unit magnet (as shown in, for example, FIG. 10). The drive unit rotates the impeller by using attracting permanent magnets arranged in a radial setup. The drive magnets 450 are driven by a motor 403 and rotate when the motor is engaged. In view of the attracting nature of the permanent magnets, the driven magnets 150 in the impeller 101 will follow, resulting in rotation of the impeller. There is no physical contact between these permanent magnets.

The bearing 480 (shown in FIG. 8A) assists in keeping the impeller radially centered. While plain bearings and ball bearings (including closed ball bearings) can be used, a plain bearing is preferred since it can handle both radial and axial forces and would generate less particles during mixing in comparison to ball bearings. Additionally, plain bearings create a liquid film, essentially eliminating friction at certain speed. Because of the radial setup of the magnets and the location of the bearing, the force applied to the bearing is minimal because the play in the bearing is minimal. Force on the bearing will increase with more play. Axial positioning and stability is provided by the centering forces of the magnets, which eliminate the need for axial bearings.

In an embodiment of the invention, an embodiment of the agitator is arranged in a container, providing an embodiment of a mixing vessel for use in bioprocessing comprising a biocontainer comprising a closed container (typically a flexible container such as a plastic container) having an interior volume suitable for containing fluid, the container comprising a bottom wall having an interior surface and an exterior surface, a top wall, at least one side wall, the side wall(s) being joined to the top wall and the bottom wall; and at least one inlet port, and at least one drain port, the at least one drain port being arranged in the bottom wall; and, the embodiment of the agitator, wherein the flange is mounted (e.g., welded) to the interior surface of the bottom wall. The mixing vessel is designed for single use (e.g., in a tote (sometimes referred to as a tank)), so after use, the biocontainer and agitator can be discarded.

A variety of closed containers are suitable for use in embodiments of the invention, and suitable containers are known in the art. A variety of container shapes (e.g., cylindrical, cuboid, hexagonal) and container volumes are suitable for use in embodiments of the invention.

FIGS. 11 and 12 show an illustrative tote 1000 for receiving a missing vessel, wherein FIG. 13 shows a partial detail view of an embodiment of a mixing vessel 500. FIG. 11 shows a bottom view of the tote, also showing the motor 403 of the drive unit. While FIG. 11 shows a hexagon shaped tank with a fixed drive unit, other arrangements (e.g., a cubical tank and/or a removable drive unit on a trolley) are suitable for carrying out embodiments of the invention.

FIG. 12 shows a cross-sectional view of the tote with mixing vessel along line 12-12 of FIG. 11, and FIG. 13 shows a partial detail view of FIG. 12. The illustrated embodiment of the mixing vessel 500 comprising a biocontainer 501 comprising a closed container having an interior volume suitable for containing fluid, the container comprising a bottom wall 510 having an interior surface 510A and an exterior surface 510B, a top wall 511, at least one side wall 512, the side wall(s) being joined to the top wall and the bottom wall; and at least one inlet port 530, and at least one drain port 531, the at least one drain port being arranged in the bottom wall; and, the embodiment of the agitator, wherein the flange 210 is mounted (e.g., welded) to the interior surface of the bottom wall.

While the use of a support is optional, FIGS. 12 and 13 illustrate an illustrate support 900, wherein the stubs of the impeller seat pass through the bottom wall of the bag and fit in corresponding holes in the support.

The impeller seat can be engaged with the locking and centering mechanism and the drive unit can be inserted before or after the biocontainer contains the fluid to be processed. Typically, the biocontainer is placed in a tote (the biocontainer may be placed on a support before placement in the tote), the seat is locked, the bag, if folded, is unfolded, biocontainer tubing is connected, the drive unit is inserted, and subsequently, the biocontainer is filled with the fluid to be processed.

Once the biocontainer contains the fluid to be processed, the drive unit can be operated to mix the contents. The mixer system and drive unit can be subsequently removed without comprising exposing the contents of the biocontainer to the outside environment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A mixer engagement system comprising:
an agitator comprising:
(a) a rotatable impeller comprising two or more blades, two or more magnets, and a shaft, wherein the impeller is configured to be driven by a drive unit magnetically coupled to the impeller;
(b) an impeller seat receiving the rotatable impeller, the impeller seat comprising an upwardly arranged cylindrical housing, a flange, and a base, the cylindrical housing comprising a central opening for the impeller shaft, and the base comprising a collar and at least 3 pins arranged to engage with a locking and centering mechanism; and,
(c) a locking and centering mechanism comprising a rotatable hollow cylindrical housing comprising at least 3 angled slots configured to receive the pins of the impeller seat, each slot comprising an open end, a downwardly angled channel, and a closed end; and
(d) a lever mounted to the rotatable hollow cylindrical housing, wherein, when the impeller seat is placed in contact with the locking and centering mechanism, with the pins in the open ends of respective slots, and the lever is in a first open position, movement of the lever from the first open position to a second closed position rotates the rotatable hollow cylindrical housing such that the pins move downwardly in the slots along the downwardly angled channels to the closed ends, locking the impeller seat into a fixed and compressed position.

2. A mixer system comprising:
the mixer engagement system of claim 1, and,
(e) a drive unit comprising a motor and two or more magnets, wherein the drive unit is removably insertable into the rotatable hollow cylindrical housing of the locking and centering mechanism, and once inserted, the drive unit can be operated to magnetically drive the impeller.

3. A mixing vessel for use in bioprocessing comprising:
a biocontainer comprising a closed container having an interior volume suitable for containing fluid, the container comprising a bottom wall having an interior surface and an exterior surface, a top wall, at least one side wall, the side wall(s) being joined to the top wall and the bottom wall; and at least one inlet port, and at least one drain port, the at least one drain port being arranged in the bottom wall; and,
the mixer engagement system of claim 1, wherein the flange of the impeller seat is mounted to the interior surface of the bottom wall.

4. A method for processing fluid comprising:
(A) obtaining a biocontainer comprising a closed container having an interior volume suitable for containing fluid, the container comprising a bottom wall having an interior surface and an exterior surface, a top wall, at least one side wall, the side wall(s) being joined to the top wall and the bottom wall; and at least one inlet port, and at least one drain port, the at least one drain port being arranged in the bottom wall; and, a mixing engagement system comprising:

an agitator comprising:

(a) a rotatable impeller comprising two or more blades, two or more magnets, and a shaft, wherein the impeller is configured to be driven by a drive unit magnetically coupled to the impeller;

(b) an impeller seat receiving the rotatable impeller, the impeller seat comprising an upwardly arranged cylindrical housing, a flange, and a base, the cylindrical housing comprising a central opening for the impeller shaft, and the base comprising a collar and at least 3 pins arranged to engage with a locking and centering mechanism, wherein the flange is mounted to the interior surface of the bottom wall of the container;

and, (c) a locking and centering mechanism comprising a rotatable hollow cylindrical housing comprising at least 3 angled slots configured to receive the pins of the impeller seat, each slot comprising an open end, a downwardly angled channel, and a closed end; and (d) a lever mounted to the rotatable hollow cylindrical housing, wherein, when the impeller seat is placed in contact with the locking and centering mechanism, with the pins in the open ends of respective slots, and the lever is in a first open position, movement of the lever from the first open position to a second closed position rotates the rotatable hollow cylindrical housing such that the pins move downwardly in the slots along the downwardly angled channels to the closed ends, locking the impeller seat into a fixed and compressed position;

(B) moving the lever from the first open position to the second closed position and engaging the impeller seat with the locking and centering mechanism;

(C) inserting a removable drive unit comprising a motor and two or more magnets into the rotatable hollow cylindrical housing of the locking and centering mechanism, and, once the biocontainer contains fluid to be processed, operating the drive unit to magnetically drive the impeller and mix the fluid in the biocontainer.

* * * * *